(12) United States Patent
Lee et al.

(10) Patent No.: US 8,157,564 B2
(45) Date of Patent: Apr. 17, 2012

(54) MANUFACTURING METHOD AND APPARATUS OF ARTIFICIAL TEETH USING DENTAL CT

(75) Inventors: Sang Chul Lee, Gyeonggi-Do (KR); Chang Hwan Byun, Seoul (KR); Tae Seok Park, Gyeonggi-Do (KR)

(73) Assignee: Ray Co., Ltd., Gyeonggi-Do (KR)

( * ) Notice: Subject to any disclaimer, the term of this patent is extended or adjusted under 35 U.S.C. 154(b) by 228 days.

(21) Appl. No.: 12/515,404

(22) PCT Filed: Aug. 29, 2007

(86) PCT No.: PCT/KR2007/004168
§ 371 (c)(1),
(2), (4) Date: May 18, 2009

(87) PCT Pub. No.: WO2008/062938
PCT Pub. Date: May 29, 2008

(65) Prior Publication Data
US 2010/0055647 A1 Mar. 4, 2010

(30) Foreign Application Priority Data
Nov. 21, 2006 (KR) .................. 10-2006-0115187

(51) Int. Cl.
*A61C 8/00* (2006.01)

(52) U.S. Cl. ....................... 433/223; 433/173
(58) Field of Classification Search ............. 433/223, 433/173, 213
See application file for complete search history.

(56) References Cited

U.S. PATENT DOCUMENTS

| 4,837,732 | A | * | 6/1989 | Brandestini et al. | 433/29 |
| 4,937,928 | A | * | 7/1990 | van der Zel | 29/896.1 |
| 6,103,321 | A | | 8/2000 | Fujinami et al. | |
| 6,354,836 | B1 | * | 3/2002 | Panzera et al. | 433/215 |
| 6,835,066 | B2 | * | 12/2004 | Iiyama et al. | 433/223 |
| 2002/0018981 | A1 | * | 2/2002 | Andersson et al. | 433/223 |
| 2002/0059049 | A1 | | 5/2002 | Bradbury et al. | |
| 2005/0261795 | A1 | * | 11/2005 | Ghosh et al. | 700/118 |
| 2006/0099552 | A1 | | 5/2006 | van der Zel et al. | |
| 2006/0111806 | A1 | * | 5/2006 | Kraemer et al. | 700/117 |
| 2007/0020582 | A1 | | 1/2007 | Neumeyer | |
| 2008/0090208 | A1 | * | 4/2008 | Rubbert | 433/173 |

FOREIGN PATENT DOCUMENTS

| WO | 97/49524 A1 | 12/1997 |
| WO | 2004/021921 A1 | 3/2004 |
| WO | 2004/054464 A2 | 7/2004 |

* cited by examiner

*Primary Examiner* — Ralph Lewis
(74) *Attorney, Agent, or Firm* — Patent Law Group LLP; Carmen C. Cook

(57) ABSTRACT

The present invention discloses a manufacturing method and apparatus of artificial human teeth using dental CT. The method comprises the steps of: removing a damaged part of human teeth; obtaining surface coordinates of the teeth using a dental CT machine located at a dental clinic for a medical checkup; converting the surface coordinates of the actual teeth to CAD/CAM data; manufacturing artificial teeth by cutting metal or ceramic with a three-dimensional N/C machine using the converted data; obtaining shape data of upper or lower actual teeth corresponding to the artificial teeth; changing the shape of the artificial teeth by direct surface processing according to the shape data of the upper or lower teeth; and coating ceramic to the artificial teeth after sintering the processed artificial teeth for a predetermined period.

3 Claims, 3 Drawing Sheets

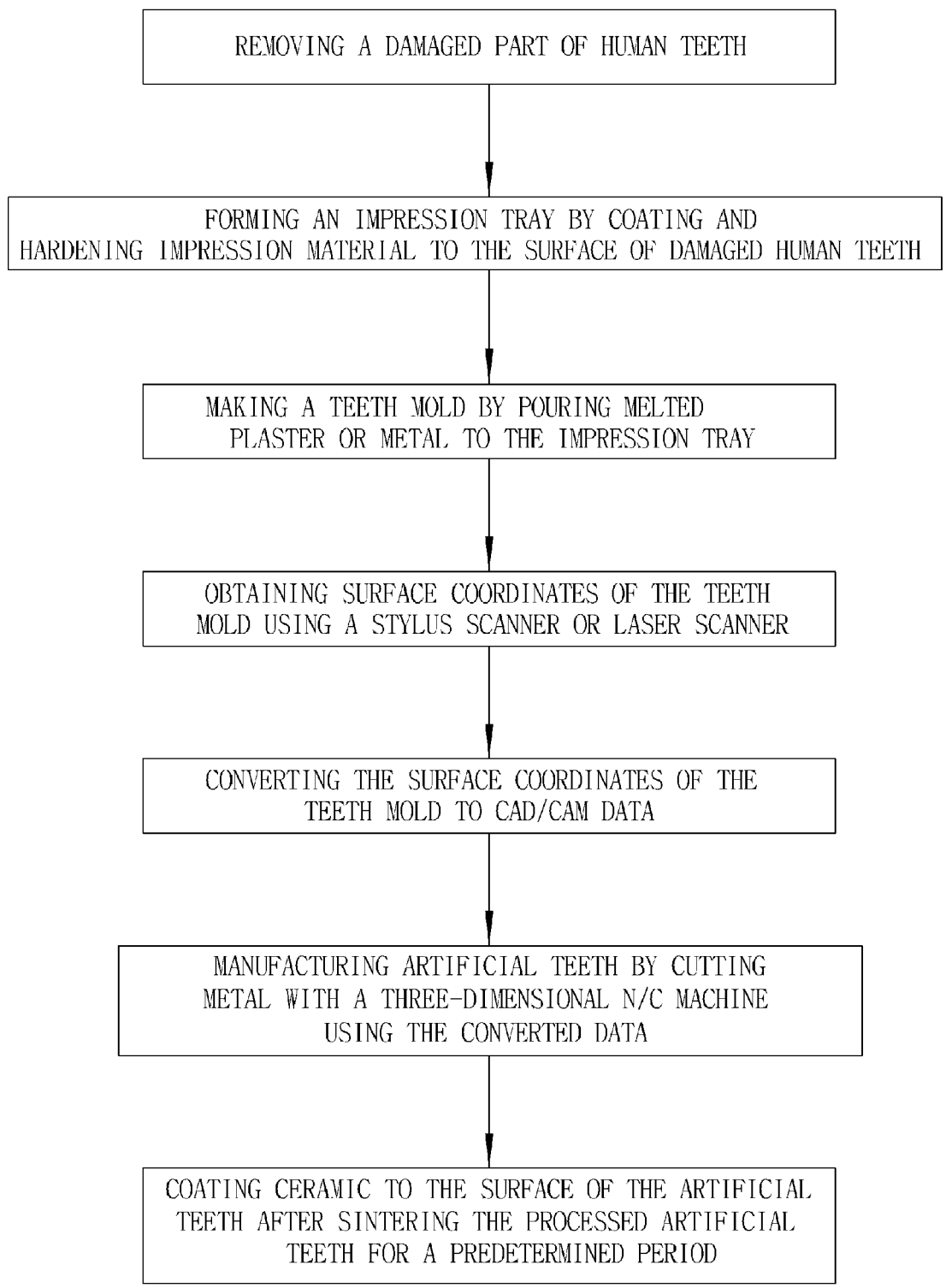

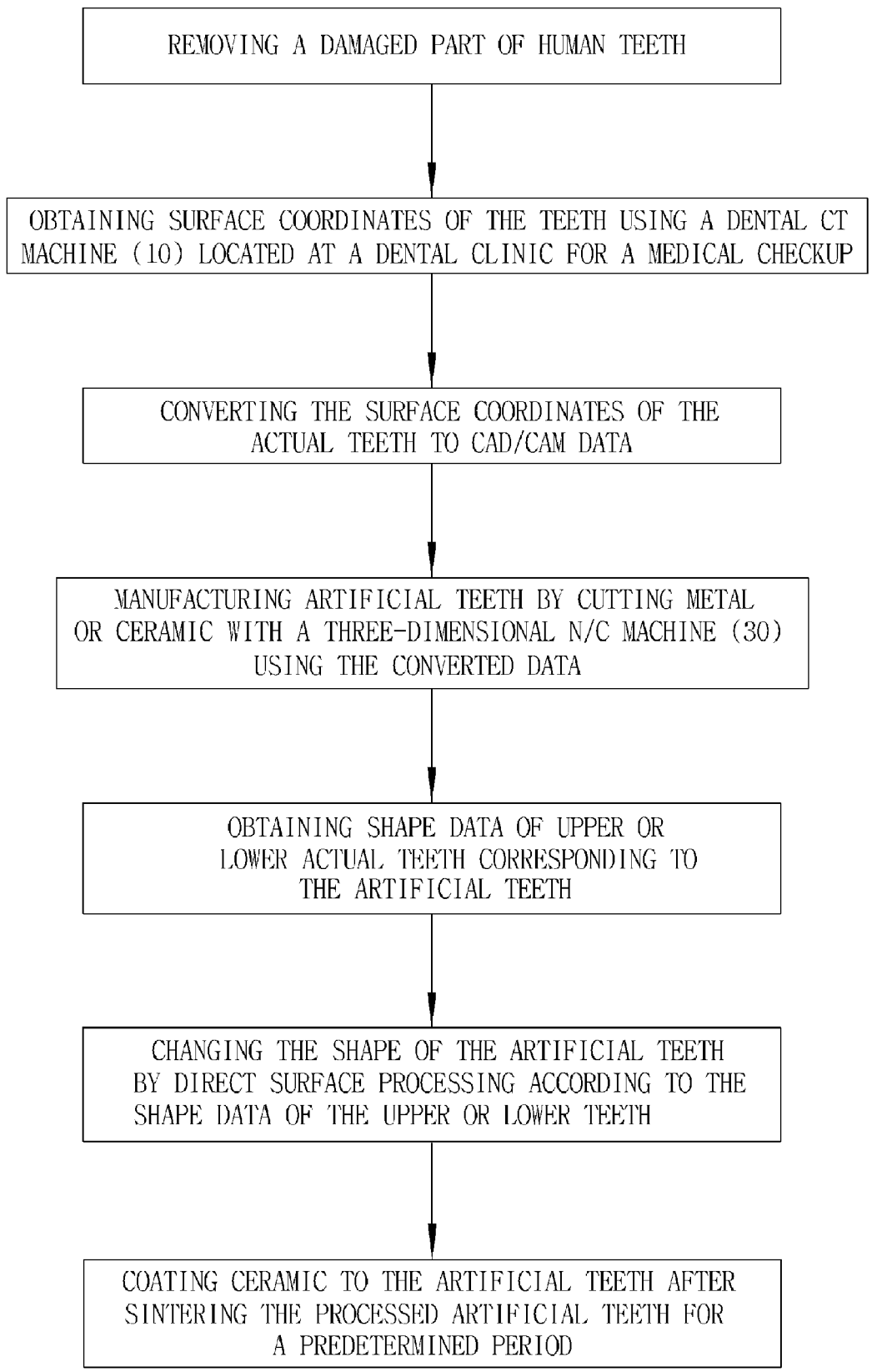

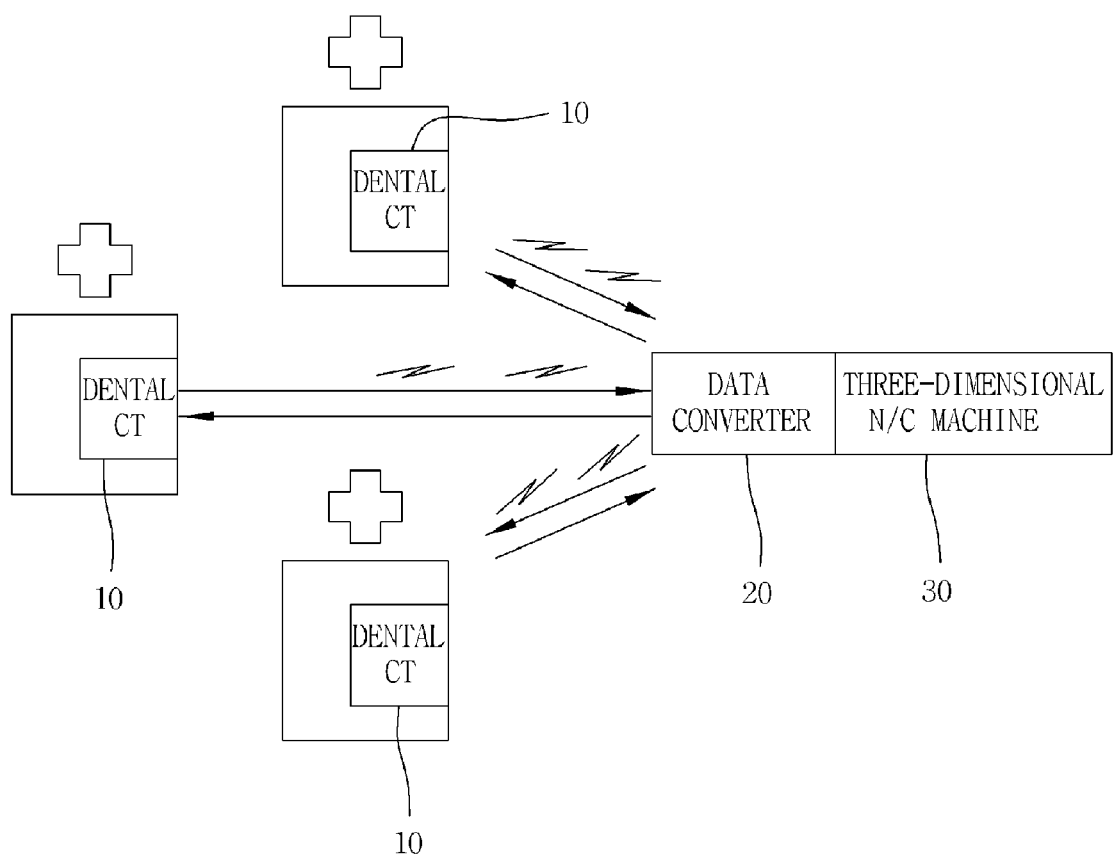
[Fig. 3]

MANUFACTURING METHOD AND APPARATUS OF ARTIFICIAL TEETH USING DENTAL CT

TECHNICAL FIELD

The present invention is directed to a manufacturing method and apparatus of artificial teeth using dental CT (Computerized Tomography) and, more specifically, to a manufacturing method and apparatus of artificial teeth that can be attached to damaged human teeth after removing a damaged part, minimizing error influence accumulated during manufacturing processes by obtaining necessary data directly from actual teeth of a patient.

BACKGROUND ART

A general manufacturing method of artificial human teeth, as shown in FIG. 1, comprises the steps of: removing a damaged part of human teeth; forming an impression tray by coating and hardening impression material to the surface of damaged human teeth; making a teeth prototype by pouring melted plaster or metal to the impression tray; obtaining surface coordinates of the teeth prototype using a stylus scanner or laser scanner; converting the surface coordinates of the teeth prototype to CAD/CAM data; manufacturing artificial teeth by cutting metal with a three-dimensional N/C(Numerical Control) machine using the converted data; and coating ceramic to the surface of the artificial teeth after sintering the processed artificial teeth for a predetermined period.

According to the above-mentioned manufacturing method of artificial teeth, the artificial teeth covering damaged teeth can be manufactured to correspond to the shape of human teeth by manufacturing the artificial teeth with a three-dimensional N/C machine. Hereinafter, a conventional manufacturing method of artificial teeth will be explained.

To begin with, nerve tissue of teeth is healed at a dental clinic and the surface of the damaged teeth is removed. Then, impression material is coated to the surface of the damaged teeth. After the impression material is hardened, a impression tray can be obtained by taking off the hardened impression material from the actual teeth. Next, the impression tray is moved to a dental laboratory where artificial teeth are manufactured. At the dental laboratory, a teeth prototype having the same shape with the grinded actual teeth is manufactured by pouring melted plaster or metal to the impression tray.

After the teeth prototype is manufactured, a stylus scanner or laser scanner scans the teeth prototype. Through this scanning process, surface coordinates of the teeth prototype can be obtained. Subsequently, the surface coordinates of the teeth prototype is converted to CAD/CAM data, and artificial teeth are manufactured by cutting metal with a three-dimensional N/C machine using the converted data.

After the artificial teeth are manufactured, the artificial teeth are sintered for a predetermined period, and ceramic is coated to the surface of the artificial teeth to make the artificial teeth similar to the actual human teeth. Then, the artificial teeth are moved to a dental clinic, and the artificial teeth are attached to the actual teeth of a patient using a bond etc. Through these processes, dental treatment for a patient is finished.

DISCLOSURE OF INVENTION

Technical Problem

However, the above-mentioned conventional manufacturing method of artificial teeth is problematic in that manufacturing cost increases and productivity decreases because of complicated manufacturing process, and a patient has to visit a dental clinic many times during manufacturing process to make sure that the artificial teeth are harmonized with the actual teeth. This causes inconvenience to a patient.

According to the conventional method, first of all, an impression tray and a teeth prototype should be manufactured. Also, artificial teeth are processed on the basis of surface coordinates of a teeth prototype after scanning the teeth prototype. This is problematic in that the artificial teeth cannot be attached to the actual human teeth correctly because the accumulated manufacturing error took place at each manufacturing process may change the shape of the artificial teeth differently from that of actual human teeth.

Specifically, in case of making artificial teeth of bridge type that is connected with several teeth, three-dimensional deformation may take place. When the bridge is very long, extra fixing process is required because the deformation becomes severe and the bridge cannot be attached to the actual human teeth correctly.

The present invention has been conceived to solve the above-mentioned drawbacks inherent in the prior art, and an object of the present invention is to provide a manufacturing method and apparatus of artificial human teeth using dental CT that can decrease manufacturing cost by simplification of the manufacturing process and enhance productivity by manufacturing the artificial teeth by utilizing the shape of actual human teeth itself without making a impression tray and a teeth prototype.

Another object of the present invention is to provide a manufacturing method and apparatus of artificial human teeth using dental CT that can obtain the teeth data directly utilizing a dental CT machine used for a medical checkup at a dental clinic, thus enhancing the utilization of the dental CT machine, simplifying manufacturing process, minimizing accumulated error, and obtaining artificial teeth which can be attached to the actual human teeth correctly.

A further object of the present invention is to provide a manufacturing method and apparatus of artificial human teeth using dental CT that can minimize the number of visiting a dental clinic and shortening manufacturing process, thus reducing inconvenience to a patient.

Technical Solution

With these objects in view, the present invention provides a manufacturing method of artificial teeth using dental CT. The method comprises the steps of: removing a damaged part of human teeth; obtaining surface coordinates of the teeth using a dental CT machine (10) located at a dental clinic for a medical checkup; converting the surface coordinates of the actual teeth to CAD/CAM data; manufacturing artificial teeth by cutting metal or ceramic with a three-dimensional N/C machine (30) using the converted data; obtaining shape data of upper or lower actual teeth corresponding to the artificial teeth; changing the shape of the artificial teeth by direct surface processing according to the shape data of the upper or lower teeth; and coating ceramic to the artificial teeth after sintering the processed artificial teeth for a predetermined period.

The present invention also provides a manufacturing apparatus of artificial teeth using dental CT. The apparatus having a dental CT machine (10) diagnosing the status of teeth and obtaining shape data of the teeth of a patient, a data converter (20) converting surface coordinates of the teeth obtained by the dental CT machine (10) to CAD/CAM data, a three-dimensional N/C machine (30) making artificial teeth with metal or ceramic utilizing CAD/CAM data of the data converter (20) is characterized in that the data converter (20) is formed with a three-dimensional N/C machine in a single body, and the data transmission between the data converter (20) and the dental CT machine is performed via cable or wireless communication.

According to the manufacturing apparatus of artificial teeth of the present invention, the data converter (20) is connected to a plurality of dental CT machine (10) located at each dental clinic via cable or wireless communication, and the dental CT machine (10) located at each dental clinic transmits the surface coordinates data to the data converter (20) at real time.

Advantageous Effects

As described above, the manufacturing method and apparatus of artificial teeth using dental CT of the present invention provides an effect that artificial teeth can be manufactured using the shape of actual teeth without making an impression tray and teeth prototype, thus reducing manufacturing cost by simplification of manufacturing process, and enhancing productivity of artificial teeth.

Further, the manufacturing method and apparatus of artificial teeth using dental CT of the present invention provides an effect that an accumulated error can be reduced by omitting a process of making an impression tray and a process of making a teeth prototype. Therefore, the manufactured artificial teeth, especially bridge type artificial teeth, can be attached correctly to actual human teeth.

Still further, the manufacturing method and apparatus of artificial teeth using dental CT of the present invention provides an effect that exact data for manufacturing artificial teeth can be obtained at one time, thus minimizing the number of visiting a dental clinic.

Yet still further, the manufacturing method and apparatus of artificial teeth using dental CT of the present invention provides an effect that each data necessary for manufacturing various artificial teeth can be obtained from each dental clinic at real time by a data converter connected to each dental clinic via cable or wireless communication.

BRIEF DESCRIPTION OF THE DRAWINGS

FIG. 1 is a flow chart showing a manufacturing process of conventional artificial teeth.

FIG. 2 is a flow chart showing a manufacturing process of artificial teeth in accordance with the present invention.

FIG. 3 is a schematic block diagram showing a manufacturing apparatus of artificial teeth in accordance with the present invention.

BEST MODE FOR CARRYING OUT THE INVENTION

Preferred embodiments of a manufacturing method and apparatus of artificial teeth using dental CT according to the present invention will now be described in detail with reference to the accompanying drawings.

FIG. 1 is a flow chart showing a manufacturing process of conventional artificial teeth. FIG. 2 is a flow chart showing a manufacturing process of artificial teeth in accordance with the present invention. FIG. 3 is a schematic block diagram showing a manufacturing apparatus of artificial teeth in accordance with the present invention.

The manufacturing method of artificial teeth using dental CT according to the present invention comprises the steps of: removing a damaged part of human teeth; obtaining surface coordinates of the teeth using a dental CT machine (10) located at a dental clinic for a medical checkup; converting the surface coordinates of the actual teeth to CAD/CAM data; manufacturing artificial teeth by cutting metal or ceramic with a three-dimensional N/C machine (30) using the converted data; obtaining shape data of upper or lower actual teeth corresponding to the artificial teeth; changing the shape of the artificial teeth by direct surface processing according to the shape data of the upper or lower teeth; and coating ceramic to the artificial teeth after sintering the processed artificial teeth for a predetermined period.

The manufacturing apparatus of artificial teeth using dental CT according to the present invention comprises: a dental CT machine (10) diagnosing the status of teeth and obtaining shape data of the teeth of a patient; a data converter (20) converting surface coordinates of the teeth obtained by the dental CT machine (10) to CAD/CAM data; a three-dimensional N/C machine (30) making artificial teeth with metal or ceramic utilizing CAD/CAM data of the data converter (20).

According to the manufacturing apparatus of artificial teeth of the present invention, the data converter (20) is connected to a plurality of dental CT machine (10) located at each dental clinic via cable or wireless communication, and the dental CT machine (10) located at each dental clinic transmits the surface coordinates data to the data converter (20) at real time.

The three-dimensional N/C machine (30) can be equipped at each dental clinic and connected to a dental CT machine (10) directly. However, as shown in FIG. 3, it is desirable to connect the one three-dimensional N/C machine (30) with a plurality of dental CT machine (10) located at each dental clinic. At any event, surface coordinates data for making artificial teeth is transmitted to the three-dimensional N/C machine (30) at real time. Therefore, artificial teeth can be made and supplied without delay.

As a plurality of dental CT machine (10) located at each dental clinic is connected to one N/C machine (30), it is possible to manage the fabrication and supply of artificial teeth very efficiently. Thus, the productivity of artificial teeth can be greatly enhanced.

Alternatively, the three-dimensional N/C machine (30) can be connected to a plurality of dental CT machine (10) located at a different dental clinic via various cable or wireless communications. Therefore, the manufacturing process of artificial teeth can be performed efficiently by collecting transmitted data from each dental clinic located at a different place. Thus, it is possible to shorten the manufacturing time of artificial teeth, and to supply the artificial teeth to each dental clinic without delay.

The term of "dental CT machine" in this specification means a general dental CT machine used at a dental clinic for medical checkup. At present, the dental CT is only used to get necessary image information in case of implant treatment.

The present invention is characterized in that the surface coordinates of actual teeth is detected in the process of diagnosing the teeth of a patient, and the surface coordinates is transmitted to a three-dimensional N/C machine (30) at real time.

According to the present invention of a manufacturing method and apparatus of artificial teeth using dental CT, the manufacturing process can be simplified because there is no need to make impression tray and teeth prototype for making artificial teeth.

Also, the surface coordinates of actual teeth can be obtained at the time of diagnosing the teeth of a patient. Thus, a patient does not have to visit a dental clinic many times for getting artificial teeth.

Hereinafter, a process of manufacturing artificial teeth according to the present invention will be explained.

At first, the surface of damaged teeth is removed after nerve tissue is healed at a dental clinic. Then, a dental CT machine takes photographs of the healed teeth. A surface coordinates of the actual teeth can be obtained from the photograph. The surface coordinates are transmitted to a data converter (20) at real time, and the surface coordinates are converted to CAD/CAM data by the data converter (20). The three-dimensional N/C machine (30) cuts metal or ceramic using the surface coordinates and manufactures artificial teeth.

After the artificial teeth are manufactured, the shape of the artificial teeth is further modified by direct surface processing using the shape data of actual teeth that are positioned above or below the artificial teeth in the mouth of the patient. Therefore, it is possible to obtain exact artificial teeth corresponding to the actual teeth.

Thereafter, the artificial teeth are moved to a dental clinic and ceramic is coated to the artificial teeth after sintering for a predetermined period. Finally, the artificial teeth are attached to a patient's teeth by an adhesive like dental cement. Through these processes, dental treatment for a patient is finished.

While the present invention has been shown and described in respect to one preferred embodiment, this is for the illustrative purpose only and is not intended to limit the scope of the invention by no means. It will be understood by those skilled in the art that various changes and modifications may be made thereto without departing from the spirit and scope of the invention as defined in the following claims.

INDUSTRIAL APPLICABILITY

As described in the foregoing, the present invention can be applied to a manufacturing method and apparatus of artificial teeth using dental CT that can be attached to actual human teeth after removing a damaged part of the teeth.

The invention claimed is:

1. A manufacturing method of artificial teeth using dental CT (Computerized Tomography) comprising the steps of:
   removing a damaged part of human teeth;
   obtaining surface coordinates of the teeth using a dental CT machine—located at a dental clinic for a medical checkup;
   converting the surface coordinates of the actual teeth to CAD/CAM data;
   manufacturing artificial teeth by cutting metal or ceramic with a three-dimensional N/C (Numerical Control) machine using the converted data;
   obtaining shape data of actual teeth that are positioned above or below the artificial teeth;
   modifying the shape of the artificial teeth further by direct surface processing according to the shape data of the actual teeth that are positioned above or below the artificial teeth; and
   coating ceramic to the artificial teeth after sintering the processed artificial teeth for a predetermined period.

2. A manufacturing apparatus of artificial teeth using dental CT (Computerized Tomography) comprising:
   a dental CT machine diagnosing the status of teeth of a patient and obtaining shape data of the teeth, the dental CT machine being configured to obtain surface coordinates of the teeth of the patient after removal of a damaged part of the teeth and to obtain the shape data of actual teeth that are positioned above or below the artificial teeth;
   a data converter converting the surface coordinates of the teeth obtained by the dental CT machine to CAD/CAM data; and
   a three-dimensional N/C (Numerical Control) machine manufacturing the artificial teeth with metal or ceramic utilizing the CAD/CAM data of the data converter characterized in that the data converter is formed with the three-dimensional N/C machine in a single body, and the data transmission between the data converter and the dental CT is performed via cable or wireless communication,
   wherein the three-dimensional N/C machine is configured to modify the shape of the artificial teeth further by direct surface processing according to the shape data of the actual teeth that are positioned above or below the artificial teeth and to coat ceramic to the artificial teeth after sintering the processed artificial teeth for a predetermined period.

3. The manufacturing apparatus of artificial teeth according to claim 2, wherein the data converter is connected to a plurality of dental CT machines located at each dental clinic via cable or wireless communication, and the dental CT machines located at each dental clinic transmits the surface coordinates data to the data converter at real time.

* * * * *